(12) United States Patent
Verma et al.

(10) Patent No.: US 10,344,314 B2
(45) Date of Patent: Jul. 9, 2019

(54) SYSTEMS AND METHODS FOR STERILITY TESTING OF RADIONUCLIDE GENERATOR COLUMN ASSEMBLIES

(71) Applicant: Curium US LLC, St. Louis, MO (US)

(72) Inventors: Sumit Verma, Chesterfield, MO (US); Kevin B. Graves, Catawissa, MO (US); Bryan S. Petrofsky, St. Louis, MO (US); James Richard Spieker, Jr., O'Fallon, MO (US)

(73) Assignee: Curium US LLC, St. Louis, MO (US)

( * ) Notice: Subject to any disclaimer, the term of this patent is extended or adjusted under 35 U.S.C. 154(b) by 214 days.

(21) Appl. No.: 15/410,505

(22) Filed: Jan. 19, 2017

(65) Prior Publication Data

US 2017/0321244 A1 Nov. 9, 2017

Related U.S. Application Data

(60) Provisional application No. 62/331,611, filed on May 4, 2016.

(51) Int. Cl.
*C12Q 1/22* (2006.01)
*A61L 2/07* (2006.01)
*G21G 1/00* (2006.01)
*G21G 4/08* (2006.01)

(52) U.S. Cl.
CPC .............. *C12Q 1/22* (2013.01); *G21G 1/001* (2013.01); *G21G 1/0005* (2013.01); *G21G 4/08* (2013.01); *G21G 2001/0042* (2013.01)

(58) Field of Classification Search
CPC ............ C12Q 1/22; A61L 2/07; G21G 1/0005
See application file for complete search history.

(56) References Cited

U.S. PATENT DOCUMENTS

| | | | |
|---|---|---|---|
| 4,039,835 A | 8/1977 | Colombetti | |
| 7,737,415 B2 | 6/2010 | Casale et al. | |
| 8,333,952 B2 | 12/2012 | Nutt et al. | |
| 8,569,713 B2 | 10/2013 | Evers | |
| 8,822,950 B2 | 9/2014 | Evers | |
| 8,937,287 B2 | 1/2015 | Giamis | |
| 9,291,606 B2 | 3/2016 | Hansteen et al. | |
| 2011/0070158 A1 | 3/2011 | Nutt et al. | |
| 2013/0130309 A1 | 5/2013 | Nutt et al. | |
| 2015/0157743 A1 | 6/2015 | McFarland et al. | |
| 2015/0160171 A1 | 6/2015 | Anzellotti et al. | |
| 2015/0238918 A1 | 8/2015 | Khachaturian et al. | |
| 2016/0003791 A1 | 1/2016 | Lebedev et al. | |
| 2016/0026193 A1 | 1/2016 | Rhodes et al. | |

FOREIGN PATENT DOCUMENTS

EP 2546839 A1 1/2013
WO 2010132043 A1 11/2010

OTHER PUBLICATIONS

International Search Report and Written Opinions of the International Searching Authority regarding PCT/US2017/014231 dated May 22, 2017, pp. 13.

*Primary Examiner* — Sean E Conley
(74) *Attorney, Agent, or Firm* — Armstrong Teasdale LLP

(57) ABSTRACT

A method includes sterilizing a column assembly including a column having a parent radionuclide contained therein with a sterilizer. The method further includes transferring the column assembly from the sterilizer to a first clean room environment, transferring the column assembly from the first clean room environment to a second clean room environment, and collecting a sterility test sample from the column assembly within the second clean room environment.

10 Claims, 7 Drawing Sheets

SYSTEMS AND METHODS FOR STERILITY TESTING OF RADIONUCLIDE GENERATOR COLUMN ASSEMBLIES

CROSS-REFERENCE TO RELATED APPLICATIONS

This application claims priority to U.S. Provisional Patent Application Ser. No. 62/331,611, filed May 4, 2016, the disclosure of which is hereby incorporated by reference in its entirety.

FIELD

The field of the disclosure relates generally to radionuclide generators and, more particularly, to systems and methods for sterility testing of radionuclide generator column assemblies.

BACKGROUND

Radioactive material is used in nuclear medicine for diagnostic and therapeutic purposes by injecting a patient with a small dose of the radioactive material, which concentrates in certain organs or regions of the patient. Radioactive materials typically used for nuclear medicine include Technetium-99m ("Tc-99m"), Indium-111m ("In-111"), Thallium-201, and Strontium-87m, among others.

Such radioactive materials may be produced using a radionuclide generator. Radionuclide generators generally include a column that has media for retaining a long-lived parent radionuclide that spontaneously decays into a daughter radionuclide that has a relatively short half-life. The column may be incorporated into a column assembly that has a needle-like outlet port that receives an evacuated vial to draw saline or other eluant liquid, provided to a needle-like inlet port, through a flow path of the column assembly, including the column itself. This liquid may elute and deliver daughter radionuclide from the column and to the evacuated vial for subsequent use in nuclear medical imaging applications, among other uses.

Prior to use in medical applications, radionuclide generators are sterilized such that when sterile eluant is eluted through the device, the resulting elution is also sterile and suitable for injection into a patient. Additionally, column assemblies of radionuclide generators intended for use in the medical industry generally undergo sterility testing to ensure the column assemblies are sterile and suitable for producing sterile, injectable elutions.

At least some known methods of sterility testing column assemblies require an extended period of time between collection and processing of a sterility test sample, and/or excessive handling of a vial in which an elution sample is collected for use in sterility testing. These circumstances may result in false negative results and false positive results. Accordingly, a need exists for improved systems and methods for sterility testing radionuclide generators.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF SUMMARY

In one aspect, a method includes sterilizing a column assembly with a sterilizer. The column assembly includes a column having a parent radionuclide contained therein. The method further includes transferring the column assembly from the sterilizer to a first clean room environment, transferring the column assembly from the first clean room environment to a second clean room environment, and collecting a sterility test sample from the column assembly within the second clean room environment.

In another aspect, a system for producing radionuclide generators includes a sterilization station including at least one sterilizer, a radiation containment chamber adjoining the sterilization station, and an isolator connected to the radiation containment chamber. The radiation containment chamber encloses a first clean room environment, and includes an unloader for removing a radionuclide generator column assembly from the sterilizer. The isolator encloses a second clean room environment, and includes a sterility test sample collection system for collecting a sterility test sample from the column assembly.

In yet another aspect, a method includes transferring a column assembly from a radionuclide generator production line to an isolator, collecting a sterility test sample from the column assembly within the isolator, and returning the column assembly to the radionuclide generator production line.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

Corresponding reference characters indicate corresponding parts throughout the several views of the drawings.

DETAILED DESCRIPTION

Figure 1:
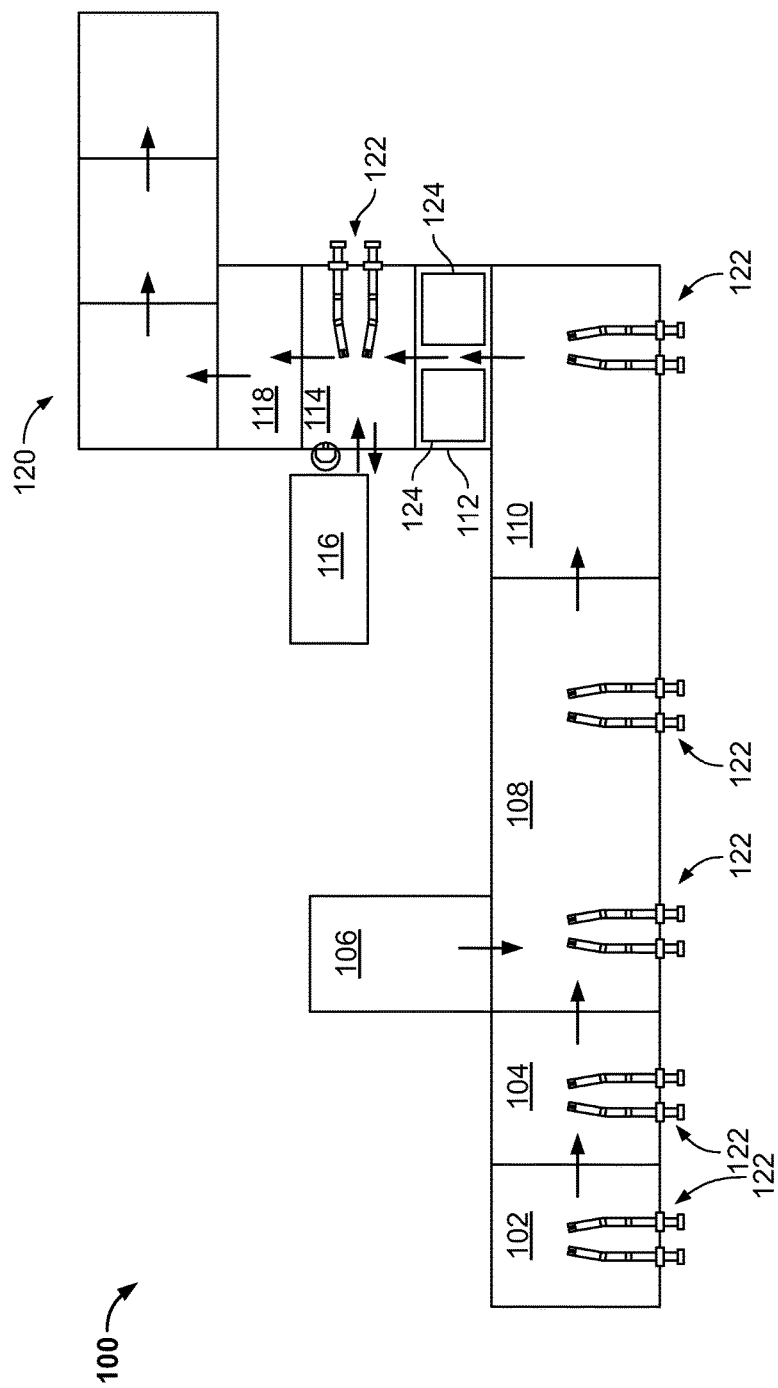
FIG. 1 is a schematic view of a system for producing radionuclide generators.

FIG. 1 is a schematic view of a system 100 for manufacturing radionuclide generators. The system 100 shown in FIG. 1 may be used to produce various radionuclide generators, including, for example and without limitation, Technetium generators, Indium generators, and Strontium generators. The system 100 of FIG. 1 is particularly suited for producing Technetium generators. A Technetium generator is a pharmaceutical drug and device used to create sterile injectable solutions containing Tc-99m, an agent used in diagnostic imaging with a relatively short 6 hour radiological half-life, allowing the Tc-99m to be relatively quickly eliminated from human tissue. Tc-99m is "generated" via the natural decay of Molybdenum ("Mo-99"), which has a 66 hour half-life, which is desirable because it gives the generator a relatively long two week shelf life. During generator operation (i.e., elution with a saline solution), Mo-99 remains chemically bound to a core alumina bed (i.e., a retaining media) packed within the generator column, while Tc-99m washes free into an elution vial, ready for injection into a patient. While the system 100 is described herein with reference to Technetium generators, it is understood that the system 100 may be used to produce radionuclide generators other than Technetium generators.

As shown in FIG. 1, the system 100 generally includes a plurality of stations. In the example embodiment, the system 100 includes a cask loading station 102, a formulation station 104, an activation station 106, a fill/wash station 108, an assay/autoclave loading station 110, an autoclave station 112, an autoclave unloading station 114, a quality control testing station 116, a shielding station 118, and a packaging station 120.

The cask loading station 102 is configured to receive and handle casks or containers of radioactive material, such as a parent radionuclide, and transfer the radioactive material to the formulation station 104. Radioactive material may be transported in secondary containment vessels and flasks that need to be removed from an outer cask prior to formulation. The cask loading station 102 includes suitable tooling and mechanisms to extract secondary containment vessels and flasks from outer casks, as well as transfer of flasks to the formulation cell. Suitable devices that may be used in the cask loading station 102 include, for example and without limitation, telemanipulators 122.

At the formulation station 104, the raw radioactive material (i.e., Mo-99) is quality control tested, chemically treated if necessary, and then pH adjusted while diluting the raw radioactive material to a desired final target concentration. The formulated radioactive material is stored in a suitable containment vessel (e.g., within the formulation station 104).

Column assemblies containing a column of retaining media (e.g., alumina) are activated at the activation station 106 to facilitate binding of the formulated radioactive material with the retaining media. In some embodiments, column assemblies are activated by eluting the column assemblies with a suitable volume of HCl at a suitable pH level. Column assemblies are held for a minimum wait time prior to charging the column assemblies with the parent radionuclide.

Following activation, column assemblies are loaded into the fill/wash station 108 using a suitable transfer mechanism (e.g., transfer drawer). Each column assembly is then charged with parent radionuclide by eluting formulated radioactive solution (e.g., Mo-99) from the formulation station 104 through individual column assemblies using suitable liquid handling systems (e.g., pumps, valves, etc.). The volume of formulated radioactive solution eluted through each column assembly is based on the desired Curie (Ci) activity for the corresponding column assembly. The volume eluted through each column assembly is equivalent to the total Ci activity identified at the time of calibration for the column assembly. For example, if a volume of formulated Mo-99 required to make a 1.0Ci generator (at time of calibration) is 'X', the volume required to make a 19.0Ci generator is simply 19 times X. After a minimum wait time, the charged column assemblies are eluted with a suitable volume and concentration of acetic acid, followed by an elution with a suitable volume and concentration of saline to "wash" the column assemblies. Column assemblies are held for a minimum wait time before performing assays on the column assemblies.

The charged and washed column assemblies are then transferred to the assay/autoclave load station 110, in which assays are taken from each column assembly to check the amount of parent and daughter radionuclide produced during elution. Each column assembly is eluted with a suitable volume of saline, and the resulting solution is assayed to check the parent and daughter radionuclide levels in the assay. Where the radioactive material is Mo-99, the elutions are assayed for both Tc-99m and Mo-99. Column assemblies having a daughter radionuclide (e.g., Tc-99m) assay falling outside an acceptable range calculation are rejected. Column assemblies having a parent radionuclide (e.g., Mo-99) breakthrough exceeding a maximum acceptable limit are also rejected.

Following the assay process, tip caps are applied to the outlet port and the fill port of the column assembly. Column assemblies may be provided with tip caps already applied to the inlet port. If the column assembly is not provided with a tip cap pre-applied to the inlet port, a tip cap may be applied prior to, subsequent to, or concurrently with tip caps being applied to the outlet port and the fill port. Assayed, tip-capped column assemblies are then loaded into an autoclave sterilizer 124 located in the autoclave station 112 for terminal sterilization. The sealed column assemblies are subjected to an autoclave sterilization process within the autoclave station 112 to produce terminally-sterilized column assemblies.

Following the autoclave sterilization cycle, column assemblies are unloaded from the autoclave station 112 into the autoclave unloading station 114. Column assemblies are then transferred to the shielding station 118 for shielding.

Some of the column assemblies are transferred to the quality control testing station 116 for quality control. In the example embodiment, the quality control testing station 116 includes a QC testing isolator that is sanitized prior to QC testing, and maintained at a positive pressure and a Grade A clean room environment to minimize possible sources of contamination. Column assemblies are aseptically eluted for in-process QC sampling, and subjected to sterility testing within the isolator of the quality control testing station 116. Tip caps are reapplied to the inlet and outlet needles of the column assemblies before the column assemblies are transferred back to the autoclave unloading station 114.

The system 100 includes a suitable transfer mechanism for transferring column assemblies from the autoclave unloading station 114 (which is maintained at a negative pressure differential, Grade B clean room environment) to the isolator of the quality control testing station 116. In some embodiments, column assemblies subjected to quality control testing may be transferred from the quality control testing station 116 back to the autoclave unloading station 114, and can be re-sterilized and re-tested, or re-sterilized and packaged for shipment. In other embodiments, column assemblies are discarded after being subjected to QC testing.

In the shielding station 118, column assemblies from the autoclave unloading station 114 are visually inspected for container closure part presence, and then placed within a radiation shielding container (e.g., a lead plug). The radiation shielding container is inserted into an appropriate safe constructed of suitable radiation shielding material (e.g., lead, tungsten or depleted uranium). Shielded column assemblies are then released from the shielding station 118.

In the packaging station 120, shielded column assemblies from the shielding station 118 are placed in buckets pre-labeled with appropriate regulatory (e.g., FDA) labels. A label uniquely identifying each generator is also printed and applied to each bucket. A hood is then applied to each bucket. A handle is then applied to each hood.

The system 100 may generally include any suitable transport systems and devices to facilitate transferring column assemblies between stations. In some embodiments, for example, each of the stations includes at least one telemanipulator 122 to allow an operator outside the hot cell environment (i.e., within the surrounding room or lab) to manipulate and transfer column assemblies within the hot cell environment. Moreover, in some embodiments, the system 100 includes a conveyance system to automatically transport column assemblies between the stations and/or between substations within one or more of the stations (e.g., between a fill substation and a wash substation within the fill/wash station 108).

In the example embodiment, some stations of the system 100 include and/or are enclosed within a shielded nuclear radiation containment chamber, also referred to herein as a "hot cell". Hot cells generally include an enclosure constructed of nuclear radiation shielding material designed to shield the surrounding environment from nuclear radiation. Suitable shielding materials from which hot cells may be constructed include, for example and without limitation, lead, depleted uranium, and tungsten. In some embodiments, hot cells are constructed of steel-clad lead walls forming a cuboid or rectangular prism. In some embodiments, a hot cell may include a viewing window constructed of a transparent shielding material. Suitable materials from which viewing windows may be constructed include, for example and without limitation, lead glass. In the example embodiment, each of the cask loading station 102, the formulation station 104, the fill/wash station 108, the assay/autoclave loading station 110, the autoclave station 112, the autoclave unloading station 114, and the shielding station 118 include and/or are enclosed within a hot cell.

In some embodiments, one or more of the stations are maintained at a certain clean room grade (e.g., Grade B or Grade C). In the example embodiment, pre-autoclave hot cells (i.e., the cask loading station 102, the formulation station 104, the fill/wash station 108, the assay/autoclave loading station 110) are maintained at a Grade C clean room environment, and the autoclave unloading cell or station 114 is maintained at a Grade B clean room environment. The shielding station 118 is maintained at a Grade C clean room environment. The packaging stations 120 are maintained at a Grade D clean room environment. Unless otherwise indicated, references to clean room classifications refer to clean room classifications according to Annex 1 of the European Union Guidelines to Good Manufacturing Practice.

Additionally, the pressure within one or more stations of the system 100 may be controlled at a negative or positive pressure differential relative to the surrounding environment and/or relative to adjacent cells or stations. In some embodiments, for example, all hot cells are maintained at a negative pressure relative to the surrounding environment. Moreover, in some embodiments, the isolator of the quality control testing station 116 is maintained at a positive pressure relative to the surrounding environment and/or relative to adjacent stations of the system 100 (e.g., relative to the autoclave unloading station 114).

Figure 2:
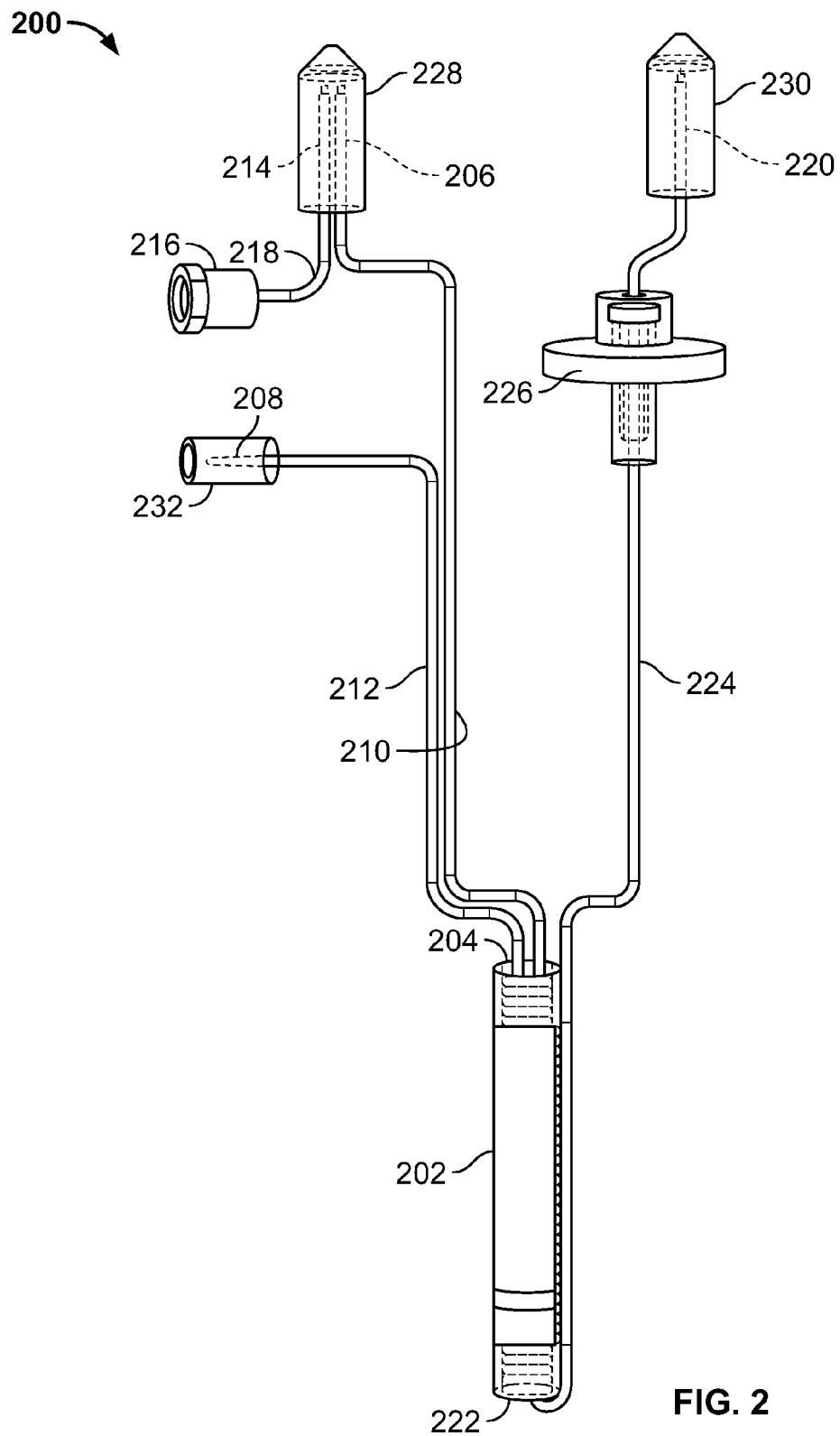
FIG. 2 is a perspective view of a column assembly of a radionuclide generator.

FIG. 2 is a perspective view of an example elution column assembly 200 that may be produced with the system 100. As shown in FIG. 2, the column assembly 200 includes an elution column 202 fluidly connected at a top end 204 to an inlet port 206 and a charge port 208 through an inlet line 210 and a charge line 212, respectively. A vent port 214 that communicates fluidly with an eluant vent 216 via a venting conduit 218 is positioned adjacent to the inlet port 206, and may, in operation, provide a vent to a vial or bottle of eluant connected to the inlet port 206. The column assembly 200 also includes an outlet port 220 that is fluidly connected to a bottom end 222 of the column 202 through an outlet line 224. A filter assembly 226 is incorporated into the outlet line 224. The column 202 defines a column interior that includes a retaining media (e.g., alumina beads, not shown). As described above, during production of the column assembly 200, the column 202 is charged via the charge port 208 with a radioactive material, such as Molybdenum-99, which is retained with the interior of the column 202 by the retaining media. The radioactive material retained by the retaining media is also referred to herein as the "parent radionuclide".

During use of the column assembly 200, an eluant vial (not shown) containing an eluant fluid (e.g., saline) is connected to the inlet port 206 by piercing a septum of the eluant vial with the needle-like inlet port 206. An evacuated elution vial (not shown) is connected to the outlet port 220 by piercing a septum of the elution vial with the needle-like outlet port 220. Eluant fluid from the eluant vial is drawn through the elution line, and elutes the column 202 containing parent radionuclide (e.g., Mo-99). The negative pressure of the evacuated vial draws eluant from the eluant vial and through the flow pathway, including the column, to elute daughter radionuclide (e.g., Tc-99m) for delivery through the outlet port 220 and to the elution vial. The eluant vent 216 allows air to enter the eluant vial through the vent port 214 to prevent a negative pressure within the eluant vial that might otherwise impede the flow of eluant through the flow pathway. After having eluted daughter radionuclide from the column 202, the elution vial is removed from the outlet port 220.

The column assembly 200 shown in FIG. 2 is shown in a finally assembled state. In particular, the column assembly 200 includes an inlet cap 228, an outlet cap 230, and a charge port cap 232. The caps 228, 230, 232 protect respective ports 206, 214, 220, and 208, and inhibit contaminants from entering the column assembly 200 via the needles.

Prior to final packaging, elution column assemblies of radionuclide generators intended for use in the medical industry are sterilized such that when sterile eluant is eluted through the device, the resulting elution is also sterile and suitable for injection into a patient. Known methods of sterilizing column assemblies include aseptic assembly, and autoclave sterilization of a vented column assembly. Aseptic assembly generally includes sterilizing components of the column assembly separately, and subsequently assembling the column assembly in an aseptic environment. Autoclave sterilization generally includes exposing a vented column assembly, having a column loaded with parent radionuclide, to a saturated steam, or a steam-air mixture environment.

Elution column assemblies of radionuclide generators intended for use in the medical industry generally undergo sterility testing to ensure the column assemblies are sterile and suitable for producing sterile, injectable elutions. Suitable methods for sterility testing elution column assemblies include membrane filtration and direct inoculation. Direct inoculation generally involves transferring elution from an eluted vial using a syringe into a test tube containing growth media (also referred to as culture media), and incubating the test tube to determine if any viable microbial organisms exist.

In membrane filtration sterility testing, a column assembly is eluted, and the eluted product liquid is passed through a sterile plastic canister containing a sterilizing filter at the canister outlet. If viable microorganisms exist in the product liquid, they are retained by the sterilizing filter inside the canister. The canister is then filled with suitable growth media (e.g., soybean-casein digest medium (TSB) or fluid thioglycollate medium (FTM)), and incubated at a target temperature for approximately 2 weeks to promote growth of any existing microbial life retained by the canister.

Figure 3:
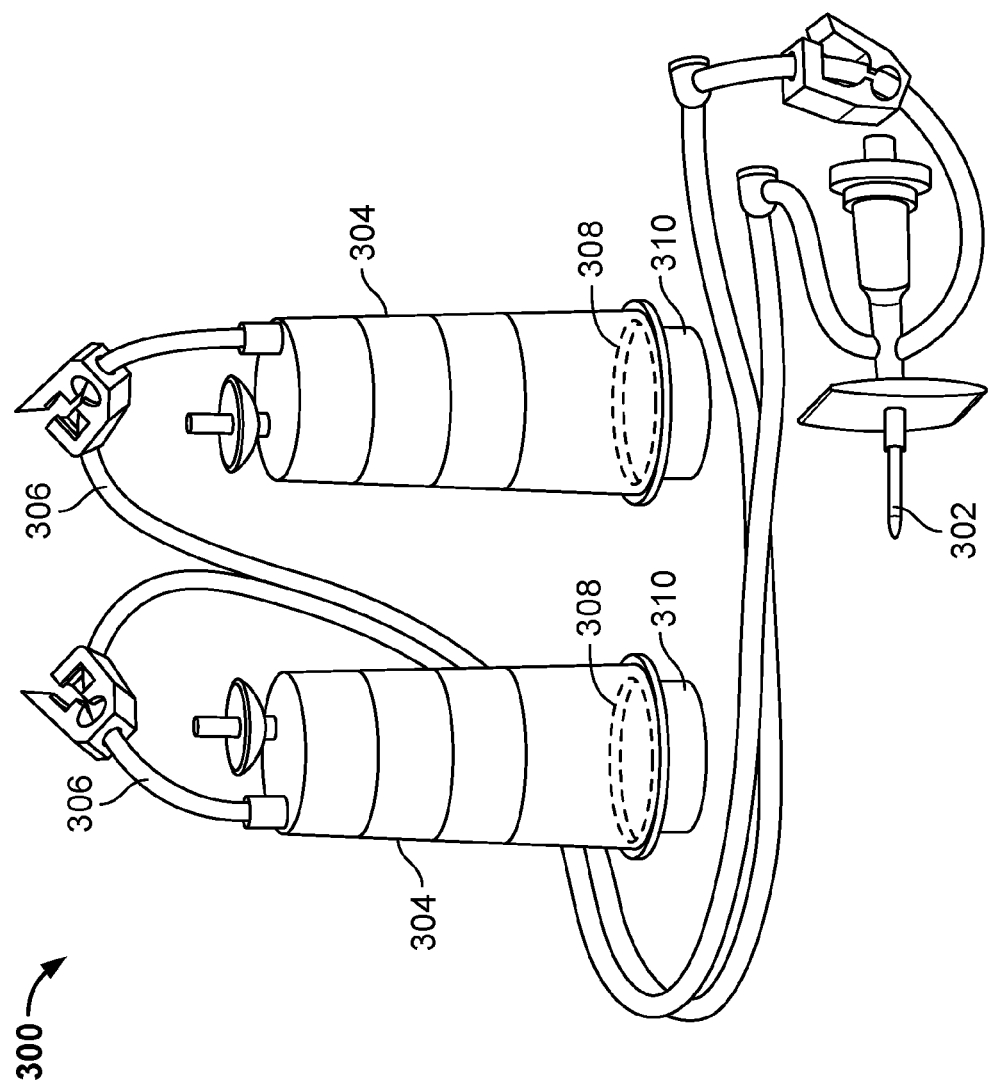
FIG. 3 is a perspective view of an example sterility test collection kit.

FIG. 3 is a perspective view of an example sterility test collection kit 300. The example sterility test collection kit 300 includes an inlet needle 302 fluidly connected to two collection canisters 304 via separate fluid conduits 306, and each collection canister 304 includes a membrane filter 308 at a corresponding canister outlet 310 for retaining microbial life. To collect a sterility test specimen from an eluted vial, the inlet needle 302 is fluidly connected to the vial by piercing a septum of the inverted vial, and draining fluid from the vial into the collection canisters 304. A pump (e.g., a peristaltic pump) may be used to facilitate pumping fluid from the vial into the collection canisters 304.

Collecting a sterility test sample by membrane filtration includes eluting a column assembly into a vial, draining or otherwise passing the elution liquid into at least one sterility test canister, and filling the canister with growth media after a target number of vials have been drained. Sterility canisters are then processed via incubation at temperatures appropriate for microbial growth, and observed for growth after approximately 2 weeks.

Previous methods of sterility testing radionuclide generators, such as Tc-99m generators, included eluting the generators into vials, and transferring the punctured vials to a different location (e.g., a different lab) to collect and process sterility test liquid from the punctured vials. To collect the sterility test samples, the punctured vials are loaded into an isolator, and the isolator contents, including punctured vials, testing supplies, tools, isolator walls, gloves, etc. are sanitized with highly concentrated (30%-35%) vaporized hydrogen peroxide (VHP). Following VHP sanitization, sterility test samples are collected by draining punctured vials through sterility canisters, which are subsequently filled with growth media, sealed, incubated, and observed for growth after approximately 2 weeks. Prior sterility test samples are usually collected about 24 hours after an elution is collected. Prior sterility testing methods are susceptible to both false negative results, and false positive results. False negative sterility testing results can occur due to the amount of time required to collect and process sterility test samples (during which viable microorganisms are not incubated, and have no nutrient supply). False negative sterility testing results can also occur due to prolonged exposure to high radiation fields within the elution vial, which can destroy viable microorganisms. False positive sterility testing results can occur due to repeated handling of punctured vials in "dirty" environments.

Methods for sterility testing radionuclide generators (e.g., Tc-99m generators) during the manufacturing and assembly process of the generator are disclosed herein. For example, methods for obtaining a sterility test sample (e.g., by membrane filtration) from a radionuclide generator during the production process are disclosed herein. These methods provide several advantages over prior sterility test methods, as described in more detail herein.

Embodiments of the present disclosure facilitate immediate sterility test sample collection following sterilization and elution of radionuclide generator column assemblies. For example, embodiments of the present disclosure include sterilizing column assemblies in an autoclave, loading individual column assemblies into a tungsten transfer shield (or other suitable radiation shield, such as lead or depleted uranium), transferring the transfer shield (including the column assembly) from a negatively pressurized Grade B hot cell into a pre-sanitized, positively pressurized Grade A sterility testing isolator, removing inlet and outlet tip caps, eluting the column assembly into a sterile elution vial via sterile eluent vial (all with pre-VHP-sanitized exteriors), and immediately draining the eluted vial through at least one sterility test canister to collect the sterility test sample. Moreover, in some embodiments, tip caps are re-applied to the column assembly following sterility test sample collection, and the column assembly is re-sterilized and packaged as saleable product, or re-sterilized and re-sampled.

Figure 4:
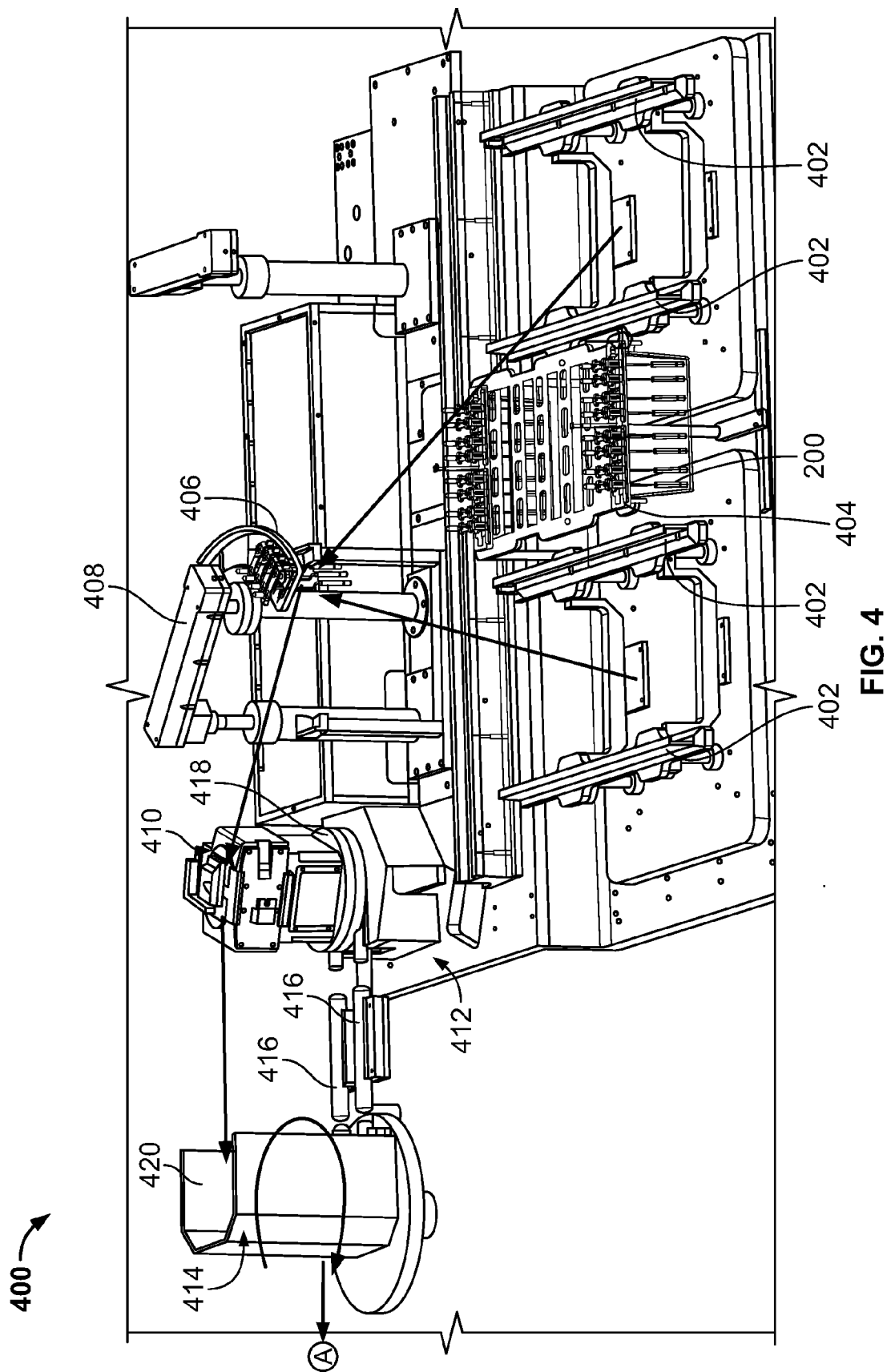
FIG. 4 is a perspective view of an example autoclave unloading station of the system shown in FIG. 1.
Figure 5:
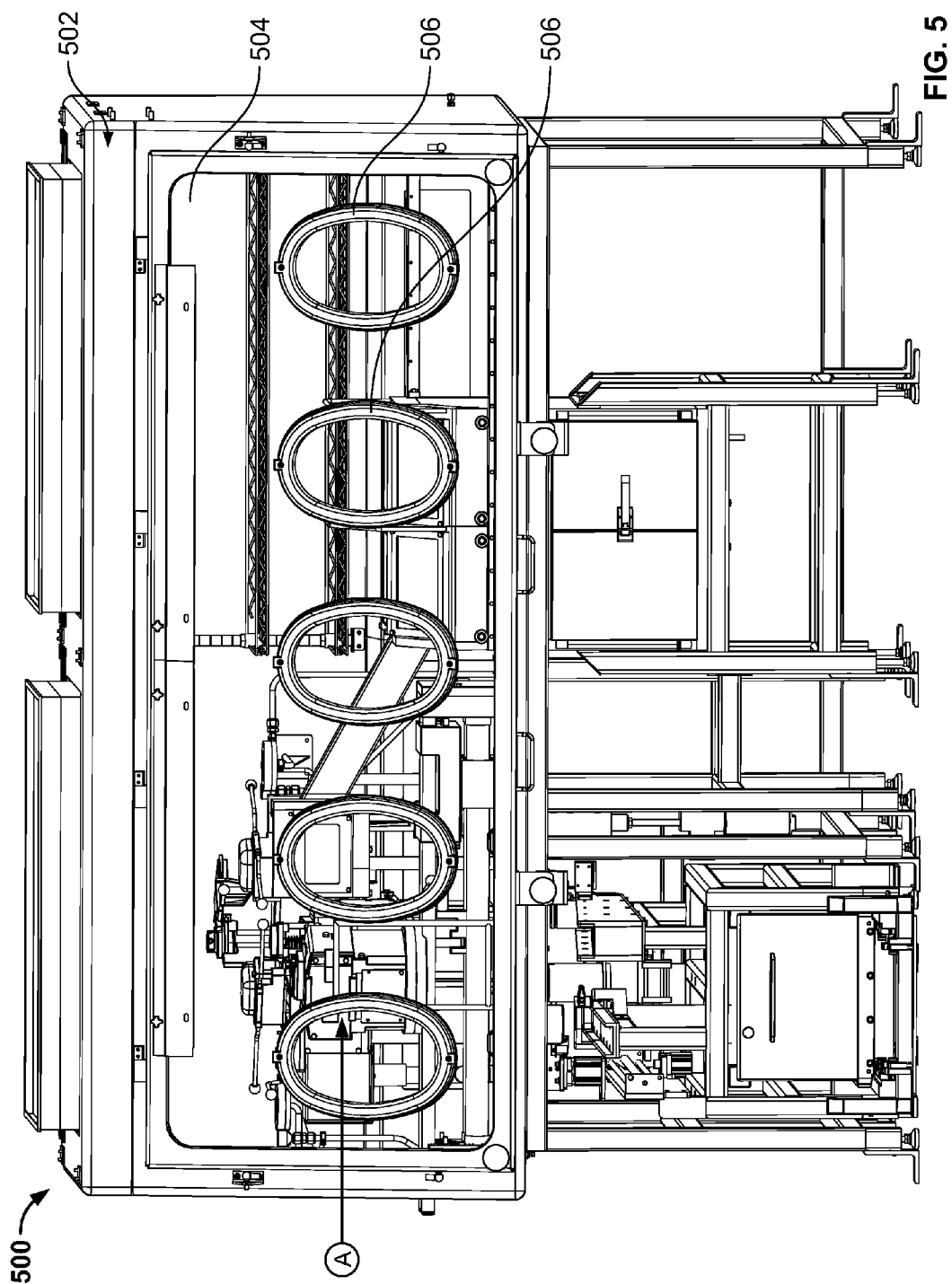
FIG. 5 is a perspective view of an isolator of a quality control testing station of the system shown in FIG. 1.
Figure 6:
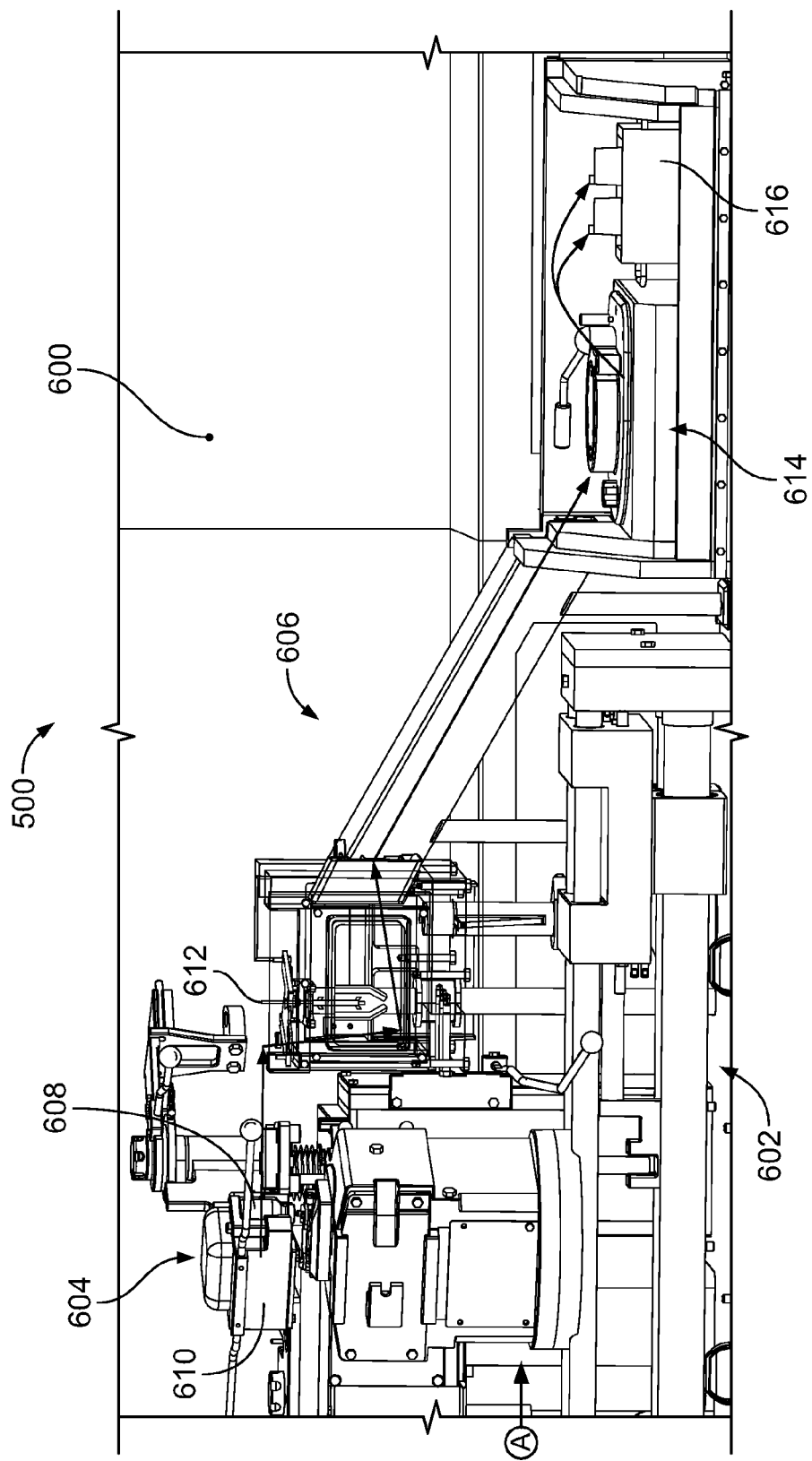
FIG. 6 is a perspective view of an interior of the isolator shown in FIG. 5.

FIG. 4 is a perspective view of an example autoclave unloading station 400 suitable for use with the system 100 of FIG. 1. FIG. 5 is a perspective view of an isolator 500 suitable for use in the quality control testing station 116 of FIG. 1. FIG. 6 is a perspective view of an interior 600 of the isolator 500. FIGS. 4-6 include arrows indicating the general process flow for collecting a sterility test sample from a column assembly.

As shown in FIG. 4, the autoclave unloading station 400 includes autoclave unloading rails 402, each positioned on the downstream (i.e., unloading) side of an autoclave sterilizer (not shown in FIG. 4). In the example embodiment, the system 100 includes two autoclave sterilizers 124 (shown in FIG. 1), and the example autoclave unloading station 400 includes two sets of autoclave unloading rails 402. Each set of the autoclave unloading rails 402 receives a cart (not shown) containing up to eight racks 404 (with up to eight column assemblies 200 per rack) from one of the autoclave sterilizers 124. The cart may be removed from the autoclave sterilizers 124, and the racks 404 transferred to an autoclave unloading shuttle 406 using an autoclave unloading mechanism including, for example and without limitation, automated, semi-automated, or manual transfer mechanisms such as telemanipulators (e.g., telemanipulators 122, shown in FIG. 1) and pneumatic cylinders.

The autoclave unloading station 400 also includes automated tooling 408 (also referred to as "pick-and-place" tooling) configured to automatically transfer one of the column assemblies 200 from one of the racks 404 positioned on the shuttle 406 to a transfer shield 410. The transfer shield 410 is constructed of suitable radiation shielding material including, for example and without limitation, tungsten, lead, and depleted uranium.

The transfer shield 410 is operatively connected to a linear slide mechanism 412 (broadly, a transfer mechanism) configured to transfer the transfer shield 410 into a rotating transfer door 414. In the example embodiment, the linear slide mechanism 412 includes a pair of parallel rails 416 that engage a base 418 of the transfer shield 410. In operation, the transfer shield 410 is pneumatically driven by a pneumatic actuator (not shown in FIG. 4), and slides along the rails 416 into the rotating transfer door 414. The base 418 of the transfer shield 410 and the rails 416 are constructed of materials that provide a low coefficient of friction between the base 418 and the rails 416 to facilitate sliding of the transfer shield 410 on the rails 416. In the example embodiment, the rails 416 are constructed of stainless steel, and the base 418 of the transfer shield 410 is constructed of PEEK (polyetheretherketone). In other embodiments, the rails 416 and the base 418 of the transfer shield 410 are constructed of any suitable materials that enable the system 100 to function as described herein.

The rotating transfer door 414 is located between the autoclave unloading station 400 and the quality control testing station 116 (shown in FIG. 1), and is configured to transfer the transfer shield 410 containing one of the column assemblies 200 between the autoclave unloading station 400 and the quality control testing station 116 (specifically, an isolator 500 of the quality control testing station 116, shown in FIG. 5). The transfer door 414 includes a cavity 420 sized and shaped to receive the transfer shield 410 therein. In FIG. 4, the transfer door 414 is shown in a first position in which the cavity 420 is open to or in communication with the autoclave unloading station 400 such that the transfer door 414 can receive the transfer shield 410 in the cavity 420. The transfer door 414 is operatively connected to a motor (not shown) that causes the transfer door 414 to rotate about a vertical axis. In some embodiments, the transfer door 414 is connected to a servo-controlled motor to precisely control rotation of the transfer door 414.

The transfer door 414 is rotatable between the first position (shown in FIG. 4) and a second position (not shown) in which the cavity 420 is open to or in communication with the interior 600 of the isolator 500. In operation, the transfer shield 410 is positioned within the cavity 420 of the transfer door 414 via the linear slide mechanism 412, and the transfer door 414 rotates from the first position to the second position such that the transfer shield 410 can be transferred to the isolator 500.

The transfer door 414 also includes radiation shielding (not shown in FIG. 4) that maintains a minimum thickness (e.g., 6 inches) of radiation shielding between the autoclave unloading station 400 and the external environment when the transfer door 414 is rotated, regardless of the angle of rotation. In other words, the shielding of the rotating transfer door 414 maintains a minimum shielding thickness along shine paths from the autoclave unloading station 400. Suitable materials from which the radiation shielding may be constructed include, for example and without limitation, lead, tungsten, and depleted uranium.

In other embodiments, the autoclave unloading station 400 may include any suitable transfer mechanism(s) that enables transfer of a column assembly 200 from the autoclave unloading station 400 to the isolator 500, including, for example and without limitation, a transfer drawer, a two door air lock system, and a telemanipulator.

Although not illustrated in FIG. 4, the components of the autoclave unloading station 400 are enclosed within a hot cell or radiation containment chamber. That is, the components of the autoclave unloading station 400 are enclosed within an enclosure constructed of nuclear radiation shielding material designed to shield the surrounding environment from nuclear radiation. Additionally, in some embodiments, the autoclave unloading station 400 is maintained at a Grade B or higher class clean room environment. That is, the autoclave unloading station 400 has a clean room classification of Grade B or higher.

The isolator 500 includes an enclosure 502 defining the interior 600 (shown in FIG. 6), and a viewing window 504 to allow an operator to view the interior 600 of the isolator 500. The isolator 500 also includes a plurality of operator access ports 506 to allow an operator to access the interior 600 of the isolator 500, and perform operations therein. The operator access ports 506 may be sealed with suitable films or barriers (not shown in FIG. 5) to provide a seal between the exterior environment and the interior 600. The interior 600 is substantially sealed from the exterior environment to provide a relatively clean environment within which to collect and process sterility test samples. Additionally, as compared to other stations of the system 100 (e.g., the autoclave unloading station 400), the isolator 500 has relatively little or no radiation shielding. In some embodiments, for example, the enclosure 502 is constructed of metals, plastics, glass, and combinations thereof. In one embodiment, the enclosure 502 is constructed of stainless steel, PEEK, and tempered glass.

Referring to FIG. 6, the isolator 500 includes a linear slide mechanism 602 configured to transfer the transfer shield 410 from the transfer door 414 and into the interior 600 of the isolator 500. In the example embodiment, the linear slide mechanism 602 is substantially identical to the linear slide mechanism 412 within the autoclave unloading station 400, and operates in substantially the same manner.

The isolator 500 also includes an elution collection apparatus 604 and a sterility test sample collection system 606 configured to collect a sterility test sample from a column assembly 200 within the transfer shield 410.

The elution collection apparatus 604 includes an eluant vial 608 and an evacuated elution vial (not shown in FIG. 6). The eluant vial 608 contains an eluant (e.g., a saline solution) which elutes the column assembly when fluidly connected thereto. The eluant vial 608 and the elution vial are held in an inverted position by a vial holder 610 configured to position and manipulate the vials to facilitate production of an elution sample and a sterility test sample. For example, the vial holder 610 is configured to position the eluant vial and the elution vial over the inlet port and the outlet port of the column assembly, respectively. The vial holder 610 can then be lowered such that each vial fluidly connects to a respective inlet or outlet port of the column assembly, thereby producing an elution sample within the elution vial. The vial holder 610 may be automated, semi-automated, or manually manipulated (e.g., through the operator access ports 506 in the isolator 500).

The sterility test sample collection system 606 includes an inlet needle 612 fluidly connected to two collection canisters via two, separate fluid conduits (not shown in FIG. 6), and a peristaltic pump 614 configured to pump fluid from the inlet needle through the conduits and into the collection canisters. The collection canisters are enclosed within a shielded container 616 constructed of suitable radiation shielding material, including, for example and without limitation, stainless steel, lead, and tungsten. The inlet needle 612, fluid conduits, and collection canisters may have the same configuration as in the sterility test collection kit 300 shown in FIG. 3.

As shown in FIG. 6, the inlet needle 612 is oriented in a vertically upward orientation. In operation, after an elution sample is collected in the elution vial, the vial holder 610 is rotated about a vertical axis to position the elution vial over the inlet needle 612. The vial holder 610 is lowered so that the elution vial septum is pierced by the inlet needle 612, which fluidly connects the elution vial with the sterility test sample collection system 606. The contents of the elution vial are then transported to the collection canisters through the fluid conduits with the assistance of the peristaltic pump 614.

In other embodiments, the elution collection apparatus 604 may be omitted, and a column assembly 200 may be eluted directly into the collection canisters of the sterility test sample collection system 606. In some embodiments, for example, the sterility test sample collection system 606 may include a septum, instead of the inlet needle 612, that is pierceable by the needle-like outlet port 220 of the column assembly 200 to connect the column assembly 200 to the collection canisters. In such embodiments, the peristaltic pump 614 may be used to draw or "suck" eluent through the column assembly 200 and directly into the sterility test collection canisters without any intermediate vials.

Once one or more sample have been collected in the collection canisters, growth media is added to the collection canisters, and the canisters are incubated to promote the growth of any existing microbial life retained by the canisters. The eluant and elution vials are discarded, and new tip caps are applied to the inlet port and the outlet port of the column assembly.

After the sterility test sample is collected, the column assembly is transferred back to the autoclave unloading station 400 via the rotating transfer door 414. Specifically, the linear slide mechanism 602 of the isolator 500 slides the transfer shield 410 into the rotating transfer door 414 (shown in FIG. 4), and the transfer door 414 rotates from the second position (not shown) to the first position (shown in FIG. 4) such that the cavity 420 of the transfer door 414 is open to the autoclave unloading station 400.

Figure 7:
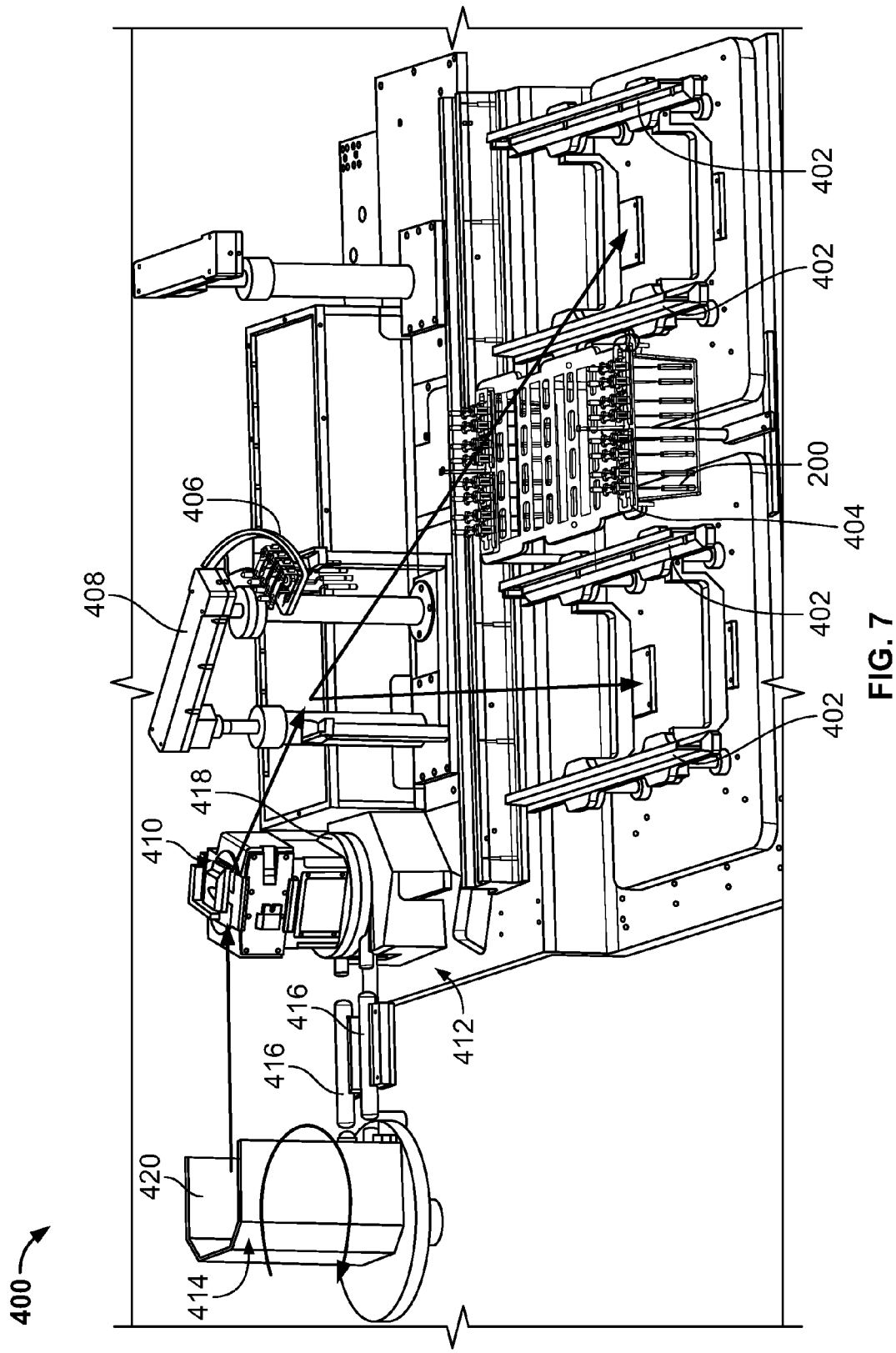
FIG. 7 is another perspective view of the autoclave unloading station shown in FIG. 4.

FIG. 7 is another perspective view of the autoclave unloading station 400, including arrows indicating the general process flow of a column assembly when the column assembly is returned to the autoclave unloading station 400 from the isolator 500. When the transfer door 414 is rotated to the first position (shown in FIG. 7), the transfer shield 410 is pulled or otherwise transferred out of the cavity 420 along rails 416, and the automated tooling 408 transfers the column assembly from the transfer shield 410 to a rack positioned on the autoclave unloading shuttle 406. In some embodiments, the column assembly is loaded into one of the autoclave sterilizers 124 (shown in FIG. 1), re-sterilized, and returned to the radionuclide generator production line. The column assembly may then be transferred back to the isolator 500 for additional sterility testing, or transferred to the shielding station 118 to be packaged for sale. In other embodiments, the column assembly may be discarded following collection of a sterility test sample.

Embodiments of the systems and methods described herein facilitate collection of a sterility test sample in a relatively clean environment, and within a relatively short amount of time following production of a sterilized column assembly. In some embodiments, for example, a sterility test sample is collected from a column assembly within 4 hours of sterilization, within 2 hours of sterilization, or even within 1 hour of sterilization. Additionally, in some embodiments, a sterility test sample is collected from a column assembly within 7 hours of the column assembly being charged with a parent radionuclide, within 5 hours of the column assembly being charged, or even within 4 hours of the column assembly being charged.

An example method of collecting a sterility test sample from a column assembly includes sterilizing a column assembly with a sterilizer (e.g., one of the sterilizers 124), the column assembly including a column having a parent radionuclide contained therein, transferring the column assembly from the sterilizer to a first clean room environment (e.g., the autoclave unloading station 400), transferring the column assembly from the first clean room environment to a second clean room environment (e.g., the isolator 500), and collecting a sterility test sample from the column assembly within the second clean room environment. In some embodiments, the first clean room environment is negatively pressurized, and the second clean room is positively pressurized. Further, in some embodiments, the first clean room environment has at least a Grade B clean room classification, and the second clean room environment has a Grade A clean room classification. Additionally, in some embodiments, such as the embodiment shown in FIGS. 4-7, a column assembly is transferred directly from the sterilizer to the first clean room environment, and directly from the first clean room environment to the second clean room environment to collect the sterility test sample.

Another example method of collecting a sterility test sample from a column assembly includes transferring a column assembly from a radionuclide generator production line to an isolator, collecting a sterility test sample from the column assembly within the isolator, and returning the column assembly to the radionuclide generator production line.

An example system suitable for carrying out methods of this disclosure includes a sterilization station (e.g., sterilization station 112) including at least one autoclave sterilizer (e.g., autoclave sterilizer 124), a hot cell or radiation containment chamber (e.g., autoclave unloading station 400) adjoining the sterilization station and enclosing a first clean room environment, and an isolator (e.g., QC sampling isolator 500) connected to the hot cell and enclosing a second clean room environment. In some embodiments, the first clean room environment has a clean room classification of Grade B or higher, and includes an autoclave unloader configured to remove the column assembly from the autoclave sterilizer. Additionally, in some embodiments, the isolator has a clean room classification of Grade A, and includes a sterility test sample collection system for collecting a sterility test sample from a radionuclide generator column assembly. Moreover, in some embodiments, the hot cell is negatively pressurized, and the isolator is positively pressurized.

The systems and methods of the present disclosure provide several advantages over known sterility testing procedures and systems. For example, embodiments of the disclosed systems and methods facilitate minimizing false negative sterility test results by reducing the time between column assembly production and sterility testing. Embodiments of the present disclosure include eluting radioactive liquid from column assemblies into vials, immediately draining the contents of the eluted vials into sterility testing canisters, adding growth media to the canisters, and incubating the canisters within a relatively short time after elution. Minimizing the time between elution collection and sterility testing facilitates detection of viable microorganisms present in the column assembly. Other methods wait up to 24 hours post-elution before starting the sterility testing process. During that time, living microorganisms present in the column assembly elution may die from lack of nutrients, or die from high background radiation present in the elution, resulting in a false negative sterility test result.

Embodiments of the disclosed systems and methods also facilitate minimizing false positive sterility test results by reducing the amount of handling and exposure to relatively dirty environments as compared to prior sterility test methods. For example, because elutions are collected and immediately drained within a sanitized Grade A environment, methods and systems of the disclosure facilitate minimizing the possibility of a false positive sterility test result caused by external contamination from repeated handling of punctured vials in dirty environments.

Additionally, the systems and methods of the present disclosure facilitate reuse of column assemblies that are used for quality control (i.e., sterility testing). For example, because new tip caps are applied to column assembly inlet and outlet ports within a Grade A clean room environment after sterility test samples are collected, the column assemblies can be re-sterilized and sold, or re-sampled in the isolator.

Additionally, embodiments of the systems and methods described herein provide an asynchronous pipeline that facilitates continued production of saleable generators even if sterility testing equipment is temporarily inoperable. For example, if sterility testing equipment or transfer equipment temporarily prevents the transfer of column assemblies from the autoclave unloading station to the sterility testing isolator, column assemblies targeted for quality control sterility sampling can be held in a buffer area (e.g., between the autoclave unloading rails shown in FIG. 4, or on a semicircular buffer near the left-most pick and place station shown in FIG. 4), while other column assemblies not targeted for QC sampling are transported to final packaging. Because the sampling pipeline is asynchronous, the system and methods facilitate minimizing delays that might otherwise impact process throughput.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A method comprising:
    sterilizing a column assembly with a sterilizer, the column assembly including a column having a parent radionuclide contained therein;
    transferring the column assembly from the sterilizer to a first clean room environment;
    transferring the column assembly from the first clean room environment to a second clean room environment; and
    collecting a sterility test sample from the column assembly within the second clean room environment.

2. The method of claim 1 including:
    transferring the column assembly directly from the sterilizer to the first clean room environment; and
    transferring the column assembly directly from the first clean room environment to the second clean room environment.

3. The method of claim 1, wherein collecting a sterility test sample includes eluting the column assembly through a collection canister including a filter.

4. The method of claim 3, further including adding growth media to the collection canister.

5. The method of claim 1, wherein sterilizing the column assembly includes exposing the column assembly to at least one of saturated steam and a steam-air mixture.

6. The method of claim 1, wherein collecting the sterility test sample includes collecting the sterility test sample from the column assembly within 4 hours of sterilizing the column assembly.

7. The method of claim 1, wherein the first clean room environment has at least a Grade B classification, and the second clean room environment has a Grade A classification.

8. The method of claim 1, wherein the first clean room environment is a negatively pressurized clean room environment, and the second clean room environment is a positively pressurized clean room environment.

9. The method of claim 1, wherein transferring the column assembly from the first clean room environment to the second clean room environment includes loading the column assembly into a transfer door located between the first and second clean room environments.

10. The method of claim 9, further including rotating the transfer door from a first position, in which an interior cavity of the transfer door is accessible from the first clean room environment, to a second position, in which the interior cavity of the transfer door is accessible from the second clean room environment.

* * * * *